United States Patent
Andresen

(10) Patent No.: US 8,513,482 B2
(45) Date of Patent: Aug. 20, 2013

(54) WOUND DRESSING

(75) Inventor: Angelica Andresen, Torslanda (SE)

(73) Assignee: Molnlycke Health Care AB, Gothenburg (SE)

(*) Notice: Subject to any disclaimer, the term of this patent is extended or adjusted under 35 U.S.C. 154(b) by 276 days.

(21) Appl. No.: 12/993,625

(22) PCT Filed: May 18, 2009

(86) PCT No.: PCT/SE2009/050555
§ 371 (c)(1),
(2), (4) Date: Nov. 19, 2010

(87) PCT Pub. No.: WO2009/145703
PCT Pub. Date: Dec. 3, 2009

(65) Prior Publication Data
US 2011/0077571 A1    Mar. 31, 2011

(30) Foreign Application Priority Data
May 29, 2008   (SE) ...................................... 0801261

(51) Int. Cl.
*A61F 13/00* (2006.01)
(52) U.S. Cl.
USPC ............................................. 602/45; 604/304
(58) Field of Classification Search
USPC ........ 604/361, 385.01, 304–309; 602/41–59; D24/189
See application file for complete search history.

(56) References Cited

U.S. PATENT DOCUMENTS

| 5,086,764 | A  |   | 2/1992  | Gilman ........................... 602/42 |
| 5,167,613 | A  |   | 12/1992 | Karami ........................... 602/42 |
| 5,759,570 | A  | * | 6/1998  | Arnold ........................... 424/443 |
| 6,051,747 | A  |   | 4/2000  | Lindqvist ........................... 602/46 |
| 6,071,267 | A  |   | 6/2000  | Zamierowski ................ 604/289 |
| 6,420,622 | B1 |   | 7/2002  | Johnston ........................... 602/41 |
| 6,492,574 | B1 | * | 12/2002 | Chen et al. ..................... 604/378 |
| 7,108,683 | B2 | * | 9/2006  | Zamierowski ................ 604/304 |
| 7,645,269 | B2 |   | 1/2010  | Zamierowski ................ 604/289 |
| 7,779,625 | B2 |   | 8/2010  | Joshi ............................... 60/313 |

(Continued)

FOREIGN PATENT DOCUMENTS

DE     19844355      4/2000
EP     0619105       10/1994

(Continued)

OTHER PUBLICATIONS

Communication and Extended European Search Report issued on Jun. 16, 2011 for European Patent Application No. EP 2282708 [Publication No. EP 20090755141], which was filed on May 18, 2009 [Inventor—Angelica Andresen; Applicant—Mölnlycke Health Care AB] [7 pages].

(Continued)

*Primary Examiner* — Patricia Bianco
*Assistant Examiner* — Tarla Patel
(74) *Attorney, Agent, or Firm* — Ballard Spahr LLP

(57) ABSTRACT

The present invention relates to a wound dressing including a first wound pad and a first cover layer covering the first wound pad and extending beyond the first wound pad around the circumference thereof. According to the invention a second wound pad is disposed outside the first cover layer and enclosed in a second cover layer. Furthermore, the first and second wound pads are connected to each other by liquid transferring means.

16 Claims, 4 Drawing Sheets

(56) References Cited

U.S. PATENT DOCUMENTS

| | | | |
|---|---|---|---|
| 7,999,870 B2 | 8/2011 | Compton | 348/308 |
| 2001/0029359 A1* | 10/2001 | Carlucci | 604/385.12 |
| 2003/0199800 A1 | 10/2003 | Levin | 602/43 |
| 2006/0020234 A1 | 1/2006 | Chou | 62/430 |
| 2008/0103462 A1 | 5/2008 | Wenzel | 604/313 |
| 2010/0262090 A1* | 10/2010 | Riesinger | 604/304 |

FOREIGN PATENT DOCUMENTS

| | | |
|---|---|---|
| EP | 1674127 | 6/2006 |
| JP | 2004-024724 | 1/2004 |
| JP | 2011-511562 | 4/2011 |
| WO | WO 01/85228 | 11/2001 |
| WO | WO 2009/075636 | 6/2009 |
| WO | WO 2009/151380 | 12/2009 |

OTHER PUBLICATIONS

Non-Final Office Action issued on Feb. 5, 2013 for Japanese Patent Application No. JP 2010-545013 [Publication No. 2011-511562], which was filed on Jan. 28, 2009 [Inventor—John Compton; Applicant—OmniVision Technologies, Inc.] [2 pages].

International Preliminary Report on Patentability and Written Opinion issued Nov. 30, 2010 for International Patent Application No. PCT/SE2009/050555, which was filed on May 18, 2009 [Inventor—Angelica Andresen; Applicant—Mölnlycke Health Care AB] [5 pages].

International Search Report issued on Sep. 7, 2009 for International Patent Application No. PCT/SE2009/050555, which was filed on May 18, 2009 [Inventor—Angelica Andresen; Applicant—Mölnlycke Health Care AB] [5 pages].

* cited by examiner

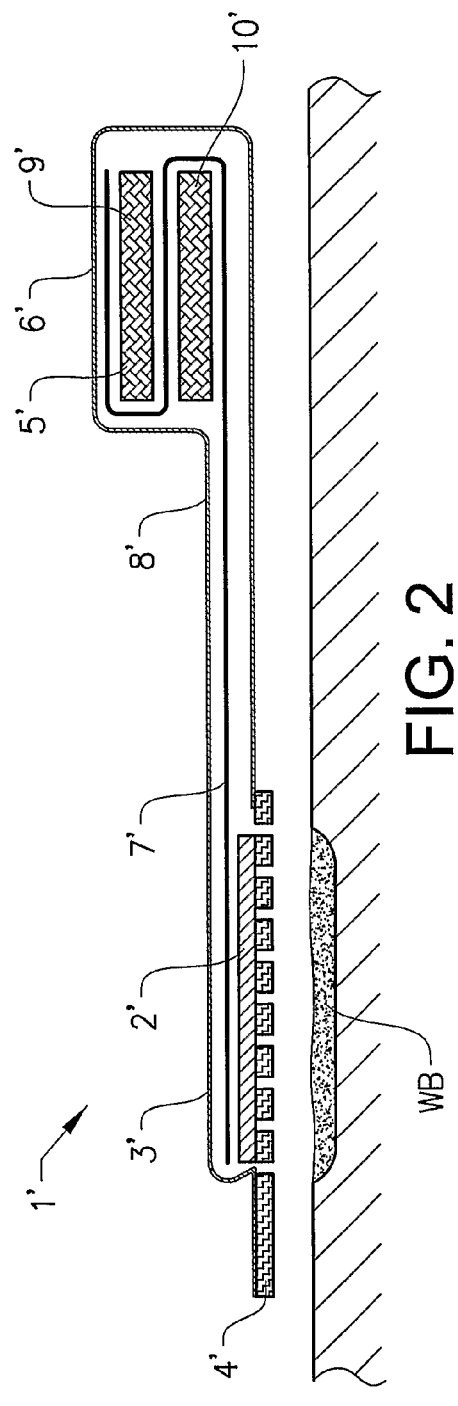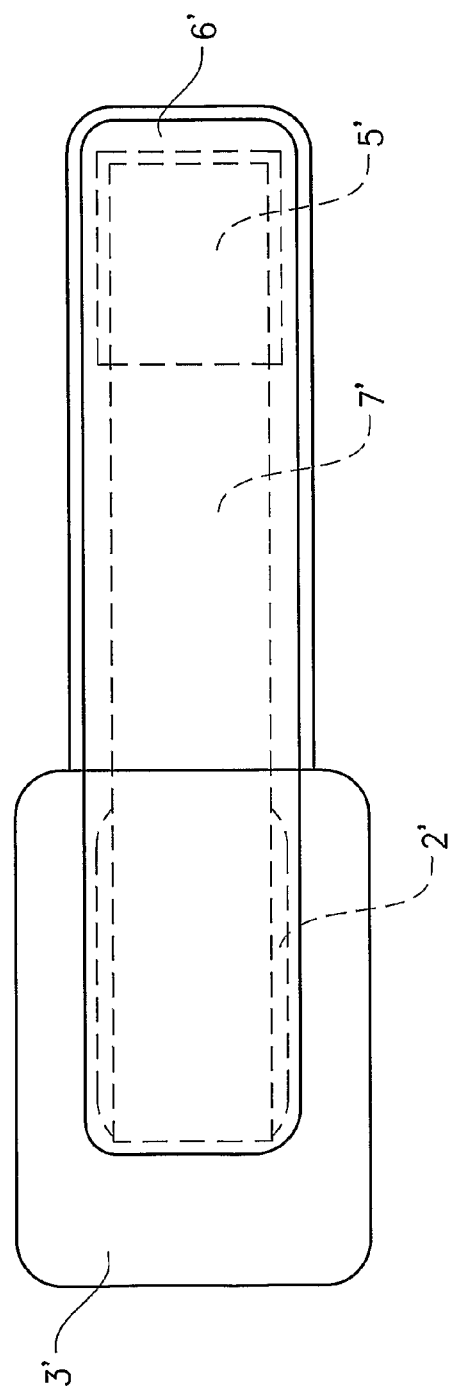

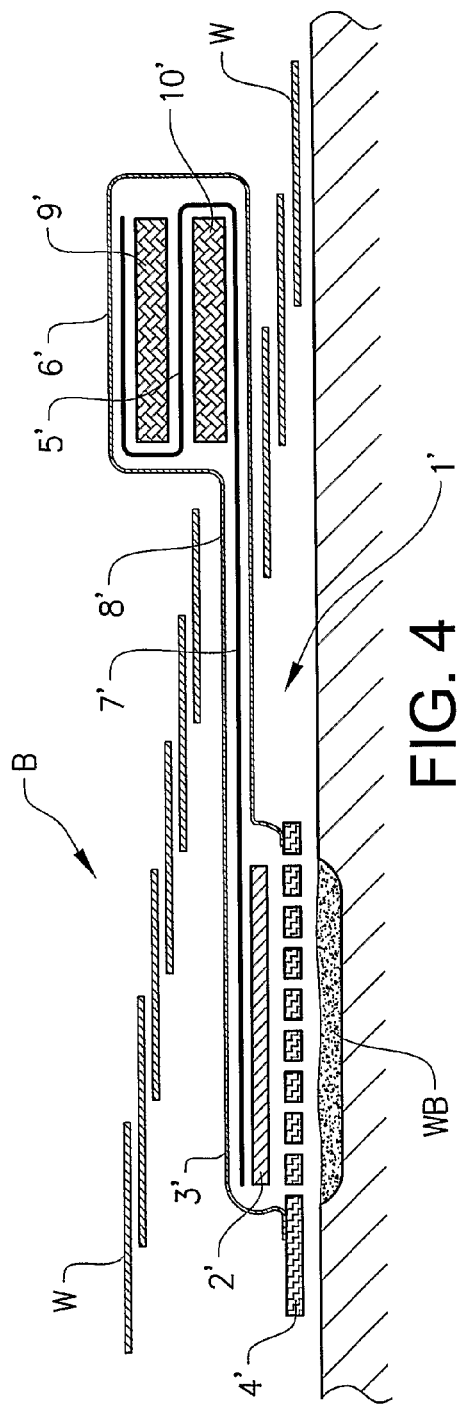
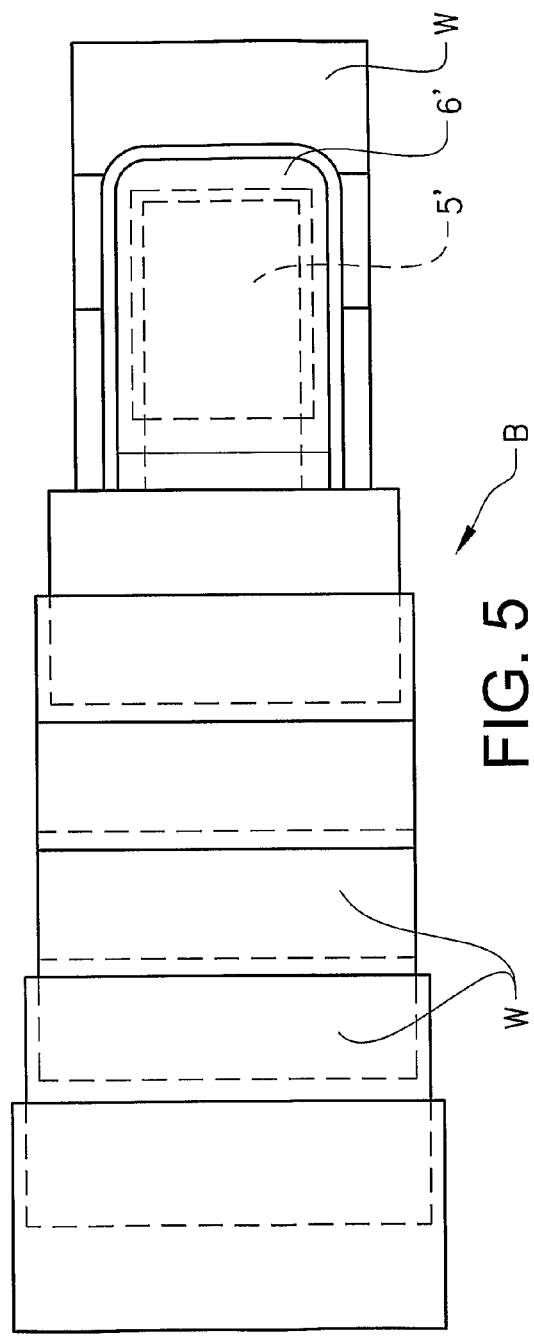

WOUND DRESSING

CROSS REFERENCE TO RELATED APPLICATIONS

The present application is a National Phase Application of International Application No. PCT/SE2009/050555, filed May 18, 2009, which claims priority to Swedish Patent Application No. 0801261-9, filed May 29, 2008, which applications are incorporated herein fully by this reference.

TECHNICAL FIELD

The present invention relates to a wound dressing including a first wound pad and a first cover layer covering the first wound pad and extending beyond the first wound pad around the circumference thereof.

BACKGROUND OF THE INVENTION

For certain wounds, such as venous leg ulcers, compression bandaging is used. In order not to damage the skin surrounding the wound bed, the wound pads used underneath the compression bandage should be thin. Dressings having thin wound pads must be changed at relatively short intervals due to the risk of leakage which is a problem since change of a compression bandage is time consuming and costly. Another problem with compression bandages is that the dressing applied to the wound is covered by an elastic bandage thereby obstructing a visual observation of the wound pad. It is therefore impossible to by visual observation of a wound pad decide when it is time to change the dressing.

The objective of the present invention is to solve the problems stated above and provide a wound dressing that can be used in combination with compression bandaging and which need not be changed at short intervals and which gives a visual indication of when a change of the wound dressing is needed.

SUMMARY OF THE INVENTION

These objectives are accomplished by a wound dressing including a first wound pad and a first cover layer covering the first wound pad and extending beyond the first wound pad around the circumference thereof, characterised in that a second wound pad is disposed outside said cover layer enclosed in a second cover layer and in that the first and second wound pads are connected to each other by liquid transferring means. By such a dressing, a compression bandage can be applied so that the first wound pad is in contact with the wound and the second wound pad could be placed outside the compression bandage connected to the first wound pad by the liquid transferring means. Due to the liquid transferring means, the second wound pad can drain the first wound pad and since the second wound pad is placed outside of the compression bandage it can function to store a lot more wound exudates than the first wound pad. Moreover, the second wound pad can be visually observed giving the viewer the possibility to decide if the dressing have to be changed or not.

In a first preferred embodiment, the first cover layer is the same integer part as the second cover layer.

In another preferred embodiment, the first and second cover layers are at least in part separate from each other.

The liquid transferring means is preferably a piece of absorbent material extending between the first and second wound pad, the end portions thereof being in contact with the respective first and second wound pad. Advantageously, said absorbent material is a hydrophilic nonwoven material or a foam with open cells.

The piece of absorbent material constituting the liquid transferring means can have smaller capillaries than said first wound pad so that the liquid transfer from the first to the second wound pad can start before the first wound pad is saturated.

Preferably, the first wound pad is, when compressed, thinner than 3 mm, preferably thinner than 2 mm, more preferably 0.5 mm. The risk for hard, compressed edges of the pad pressing against the skin of a patient when the dressing is used in combination with a compression bandage is thereby significantly reduced.

The second wound pad can contain so called super absorbent particles in order to enhance its capacity to store large quantities of wound exudates.

The second cover layer has preferably a size allowing expansion of the second wound pad due to absorption, thereby allowing the use of absorbent materials that swell during absorption.

At least the first cover layer is preferably coated by adhesive on the side thereof intended to lie against the skin of a wearer during use of the dressing.

The unit consisting of the second wound pad and at least a part of the second cover layer could advantageously be separable from the rest of the dressing in order to allow substitution of a used such unit by a fresh such unit. By such a feature there is no need to open up the compression bandage every time a certain amount of wound exudates have been absorbed in the dressing.

The invention also relates to the use of a wound dressing according to the present invention in combination with a compression bandage.

BRIEF DESCRIPTION OF THE DRAWING

The invention will now be described with reference to the enclosed figures, of which;

FIG. 3 shows a plan view from above of the wound dressing in FIG. 2, FIGS. 4 and 5 schematically show the dressing in FIG. 2 used in combination with a compression bandage in a cross-sectional and plan view, respectively, FIG. 6 schematically shows a view in cross-section of a wound dressing according to a third embodiment of the invention.

DESCRIPTION OF EMBODIMENTS

Figure 1:
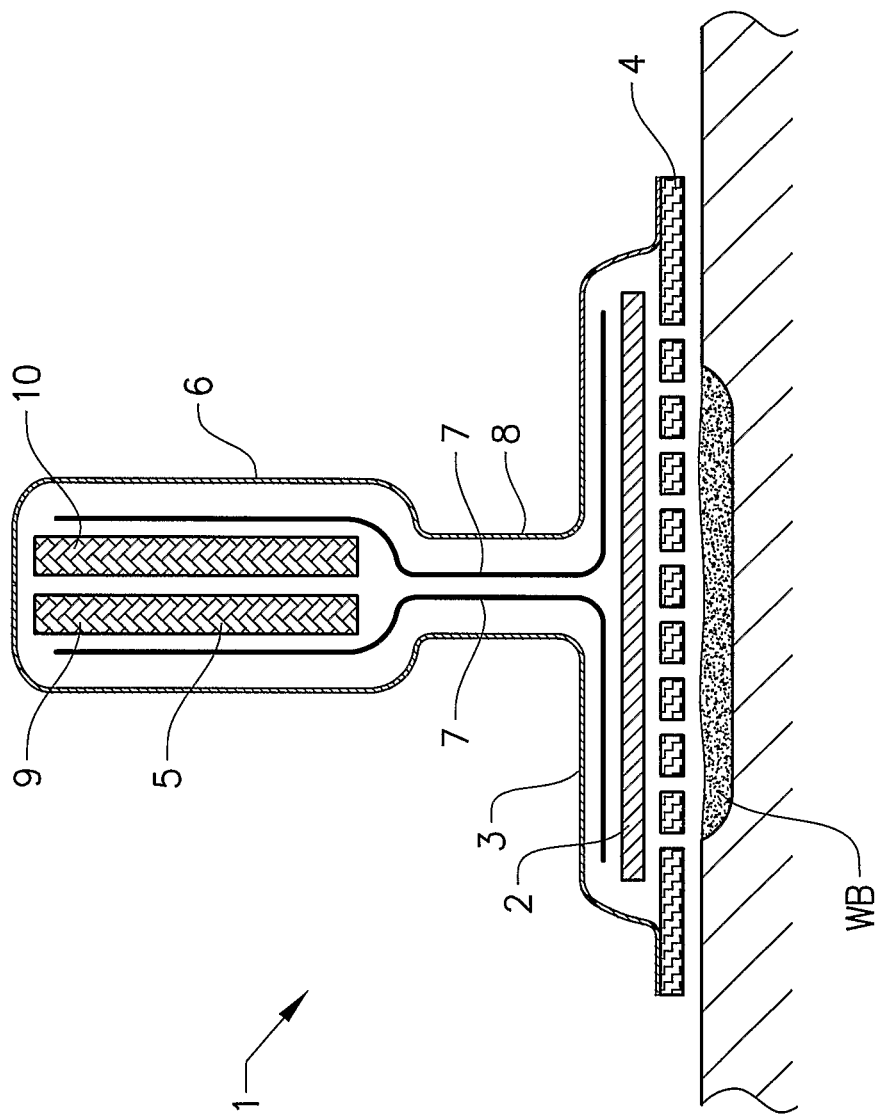
FIG. 1 schematically shows a view in cross-section of wound dressing according to a first embodiment of the invention, FIG. 2 schematically shows a view in cross-section of a wound dressing according to a second embodiment of the invention.

In FIG. 1, a sectional view of a wound dressing 1 according to a first preferred embodiment of the invention is schematically shown. The dressing 1 is shown applied to a wound bed WB. The dressing 1 includes a first wound pad 2 and a first liquid-tight cover layer 3 covering the wound pad 2 and extending beyond wound pad 2 around the circumference thereof. The first cover layer 3 is coated on the underside, i.e. the side intended to be proximate to a wound when the dressing is applied, with a layer of skin-friendly adhesive 4 at least on the parts of the cover layer extending beyond the circumference of the wound pad 2. In the shown embodiment the layer of adhesive 4 is extended also over the underside of wound pad 2, however on the underside of the wound pad the layer of adhesive 4 is discontinuous, for example applied in a pattern of spots, in order to allow wound exudates to penetrate the adhesive layer and be absorbed by the wound pad 2. Alternatively, the adhesive can be carried by a film having a pattern of holes coincident with holes in the adhesive, the edge region of such a film being affixed to cover layer 3. The pattern of holes in such a film can be extended over the whole area thereof.

According to the present invention, dressing 1 also includes a second wound pad 5. The second wound pad 5 is enclosed in a second liquid-tight cover layer 6, which in the shown embodiment has the shape of a bag. The second wound pad 5 is also fluidly connected to the first wound pad 2 by liquid transferring means 7. The liquid transferring means are in the shown example strips 7 of an absorbent material, such as a nonwoven hydrophilic material or an absorbent foam. In the first embodiment, two strips 7 of absorbent material lead from the upper side of the first wound pad 2 to the left and right side, respectively of the second wound pad 5. Also the strips 7 are enclosed in a liquid-tight cover layer 8. In the shown embodiment the cover layers 3, 6 and 8 are made in one piece from the same piece of material but they could be made of different pieces of material bonded together in a suitable way, such as by adhesive or weld bonds. The second wound pad 5 includes in the shown example two absorbent layers 9, 10 but less or more than two bodies can be included in the second wound pad. Also the first wound pad can include more than one layer of absorbent material.

In FIGS. 2 and 3, of a wound dressing 1' according to a second embodiment is schematically shown in a cross-sectional and plan view, respectively. The wound dressing 1' differs from the wound dressing 1 shown in FIG. 1 mainly in that the liquid transferring means 7' is extending sideways from the first absorbent body 2' instead of upwards therefrom as in wound dressing 1 shown in FIG. 1. Components of wound dressing 1' being similar to corresponding components in the wound dressing 1 according to FIG. 1 are given the same reference numerals with the addition of a prime sign.

In the second embodiment, the liquid transferring means 7' consists of a single strip of absorbent material which in the second absorbent body 5' encloses the two absorbent layers 9', 10' by a meander-like path. In all other aspects the second embodiment corresponds to the first embodiment shown in FIG. 1.

In FIGS. 4 and 5, the dressing 1' according to the second embodiment is schematically shown in combination with a compression bandage. The amount of pressure exerted by the bandage is determined by the amount of stretching of the bandage that is practised during winding thereof around an extremity. In FIGS. 4 and 5 parts of several windings W of such a compression bandage B is schematically shown.

As can be seen in these figures, the first wound pad 2' and its cover layer 3' are covering the wound bed WB and are in turn covered by windings W of the bandage B and thereby subjected to the pressure created by the stretching of the elastic bandage during winding thereof. In contrast thereto, the second wound pad 5' and its cover layer 6' are disposed outside of the bandage B and are thus not subjected to the pressure of in the windings W of the bandage B. In FIG. 4, the windings W are disclosed distanced from each other and from the dressing 1' but in reality the windings W would be pressed against each other and to the part of wound dressing 1' covered by windings W of bandage B. The wound pad 2' would then be compressed by the pressure provided by bandage B and its capacity for storing absorbed exudates would be significantly reduced.

The dressing 1' functions in the following way when used in a compression bandage.

Exudates from the wound bed WB will firstly be absorbed by the first wound pad 2'. When exudates absorbed by the first wound pad 2' comes into contact with the strip 7' of absorbent material, it will be absorbed therein and will after some time be transported to the second wound pad 5'. It is believed that the overpressure in the space beneath the compression bandage in relation to the atmospheric pressure inside the second wound pad promotes said transport of exudates. This transport of exudates from the first to the second wound pad will continue until the second wound pad can not store any more exudates. When this happens the dressing must be changed and the compression bandage removed. By providing a second wound pad 5' which is placed outside of the bandage B and thus not subject to the pressure from windings W thereof, several advantages are obtained in comparison with a conventional dressing containing only a first wound pad subjected to the pressure of the windings of a compression bandage. Firstly, the second wound pad 5' is not subjected to pressure from the windings W of the compression bandage B and the capacity of the second wound pad 5' to absorb and store exudates is thus not reduced by compression thereof. The wound pad 5' can therefore be designed to absorb a lot more exudates than is possible for the first wound pad 2'. Thereby, the dressing 1' need not be changed as often as a dressing containing only a first wound pad. Secondly, since the second wound pad is disposed outside the compression bandage B and not covered by the windings W thereof it is visually observable which means that a viewer, if the second cover layer is transparent, has the possibility to study the second wound pad and by visual observation judge if the dressing has to be changed or not. If the second cover layer is transparent or translucent, the amount of exudates will appear as a growing shadow on the second wound pad. The number of unnecessary changes of a dressing used in combination with a compression bandage can therefore be significantly reduced by the present invention. A third advantage is that the dressing can be designed so that the second wound pad is exchangeable per se, as will be explained later. By such a design, the compression bandage B will not need to be unwinded during the "change of dressing" so that the pressure exerted thereby is maintained during change of the second wound pad which is favourable for the healing of the wound and also reduces the time needed for change of dressing.

The dressing 1 according to the first embodiment shown in FIG. 1 could be used in the same way in a compression bandage as the dressing 1" according to the second embodiment shown in FIGS. 4 and 5. There will be no problem to wind a compression bandage so that the second wound pad 5 will be located outside the windings of the compression bandage.

Figure 6:
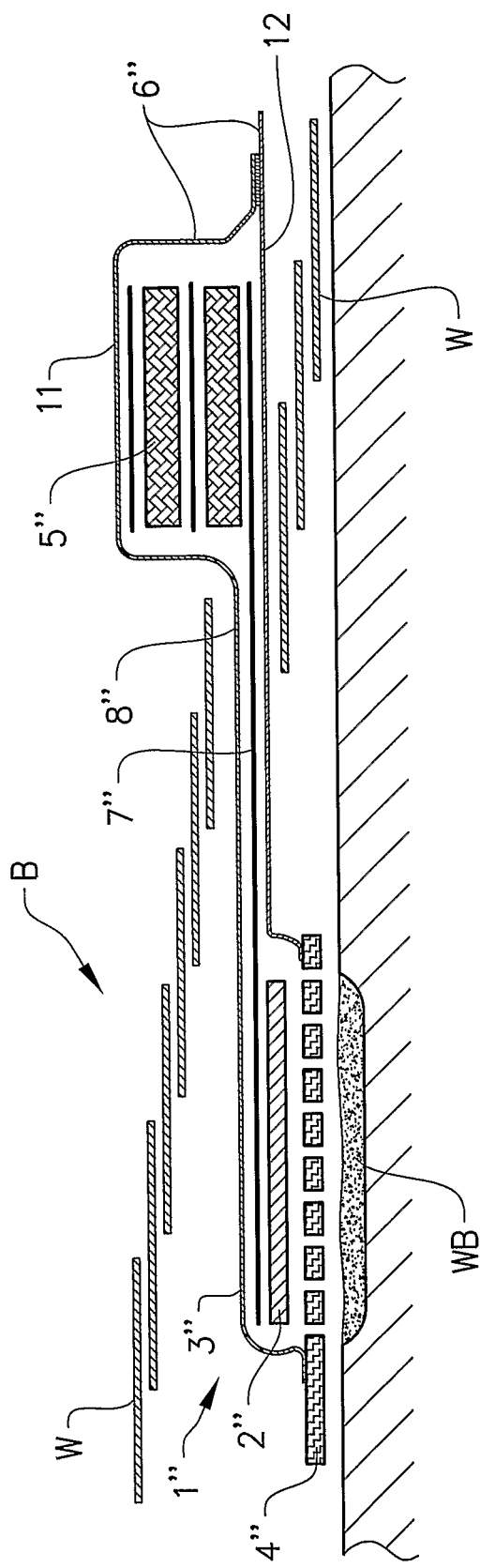

In FIG. 6, a dressing 1" according to a third embodiment is schematically shown in cross-section in combination with a compression bandage B. Dressing 1" differs from the dressing 1' according to FIGS. 4 and 5 only in the design of the second wound pad 5" and its cover layer. Components in dressing 1" similar to corresponding components in dressing 1' according to FIGS. 4 and 5 are given the same reference numerals with the addition of a bis sign.

The difference between the dressings 1' and 1" is that the wound pad 5" is exchangeable. A used wound pad 5" can thus be substituted by a fresh one. This is in the embodiment shown in FIG. 6 accomplished by dividing the second cover layer 6" for the second wound pad 5" into two separate parts 11, 12, part 11 being releasable attached to part 12 which in turn is made in one piece with cover layers 3" and 8". The releasable attachment of part 11 onto part 12 is preferably accomplished by an adhesive connection. With a dressing according to the embodiment shown in FIG. 6, the second wound pad 5" can be changed without the need to unwind the compression bandage B which is favourable for the healing of the wound and which also significantly shorten the time to "change" the dressing.

The second wound pad 5" is preferably attached to part 11 of the second cover layer 6", preferably by an adhesive connection. The second wound pad preferably has a pattern of adhesive on its underside, i.e. the side turned against part 12 of the second cover layer, in order to make good contact with the end portion of the strip 7" of absorbent material reaching into the area containing the second wound pad 5". When, during use, the second wound pad 5" is saturated or it is judged through visual observation that the second wound pad should be changed, it can be taken away by removing the unit consisting of part 11 of the second cover layer and the wound 5" and substitute this unit by a fresh such unit containing a fresh second wound pad.

In all the shown embodiments the second cover layers 6, 6' and 6" are preferably designed to enclose a larger volume than the volume of a fresh second wound pad 5, 5', 5". Thereby, the second wound pad 5,5', 5" is allowed to swell during absorption of wound exudates without being influenced by the second cover layer. The amount of such extra volume of the second cover layer can be chosen so that it is indicated that the dressing should be changed when the second wound pad had swelled to such extent that all wrinkles or folds have been smoothened out or the size thereof has been diminished to a certain extent.

The first wound pad 2, 2', 2" is preferably made of an absorbent foam material, such as polyurethane foam, for example as is referred to in U.S. Pat. No. 6,051,747. Other absorbent materials can of course be used but should preferably have relatively soft edges so that, when used in combination with a compression bandage, the edges of the wound pad do not damage the skin surrounding the wound bed. Preferably, the foam material in the first wound pad is, when compressed, thinner than 3 mm, preferably thinner than 2 mm, and more preferably thinner than 0.5 mm. The risk for hard edges of the pad pressing against the skin of a patient when the dressing is used in a compression bandage is thereby significantly reduced. The first wound pad can also consist of a nonwoven material and the liquid transferring means and the first wound pad can then be made in one piece of material.

The absorbent material used for the second wound pad can be any absorbent material known to be used in wound dressings. It can be a foam material or a body of absorbent fibres, such as cellulosic fibres, or a combination thereof when the second wound pad consists of more than one absorbent body. Advantageously, so called superabsorbent particles can be present in the second wound pad, for example in a body consisting of a mixture of cellulosic fibres and superabsorbent particles. It is also possible to build up the second wound pad of layers of superabsorbent particles separated by liquid-distribution layers. Such liquid-distribution layers can for example be of the same material as the liquid transferring strips 7,7',7" or of other absorbent materials having small capillaries.

The liquid transferring means 7,7',7" could be a nonwoven hydrophilic material or an absorbent foam. A suitable nonwoven material is Fibrella® and a suitable foam is polyurethane as exemplified above. Preferably, the absorbent material of the liquid transferring means has smaller capillaries than the absorbent material in the first wound pad The cover layers are made of plastic film, preferably a polyurethane film. Other films, such as polyethylene films, can also be used. Preferably, the films, at least for the second cover layer, should be transparent or semi-transparent, in order to enable visual observation of a wound pad. This is, however, not strictly necessary since, as explained above, there are other ways to show the condition of the wound pad covered by a cover layer.

The skin friendly adhesive is preferably a silicone adhesive but other pressure sensitive adhesives, for example hot melt adhesives, can be used. All known adhesives used in wound dressings can be used in the dressing according to the invention.

The wound dressing according to the invention has been shown and described in combination with a compression bandage. However, the inventive dressing can also have other uses. If for example a wound is located on a place on a patient where clothes sit rather tight, the first wound pad can be placed over the wound whereas the second wound pad can be disposed on a part of the patient where the clothes do not sit tight. It can also be used on locations where there is a risk for pressure sores, such as heels and buttocks.

The described embodiments can of course be modified without leaving the scope of invention. For example, instead of letting the strip 7' run in a meander-like path, separate liquid-distributing layers can be used between the two layers 9', 10' and on top of layer 9', respectively. The shape of the dressing and the wound pads therein can be different than shown in the figures. Furthermore, the pattern of adhesive on the underside of the first wound pads can be deleted. Although this skin friendly adhesive facilitates the handling of the dressings and therefore is preferred, it can be totally deleted if the dressing should be used in combination with a compression bandage since this will hold the dressing in place. The scope of invention should therefore only be limited by the content of the enclosed patent claims.

The invention claimed is:

1. A wound dressing, comprising:
a first absorbent wound pad;
a first cover layer covering the first absorbent wound pad and extending beyond the first absorbent wound pad around the circumference thereof; and
a second absorbent wound pad disposed outside the first cover layer, wherein the second absorbent wound pad is enclosed in a second cover layer, wherein the first and second absorbent wound pads are connected to each other by liquid transferring means, and wherein the liquid transferring means is flexible and extends away from the first absorbent wound pad and is absorbent.

2. The wound dressing according to claim 1, wherein said first cover layer is the same integer part as the second cover layer.

3. The wound dressing according to claim 1, wherein said first and second cover layers at least in part are separate from each other.

4. The wound dressing according to claim 1, wherein said liquid transferring means comprises a piece of absorbent material extending between the first and second absorbent wound pads, the end portions of the liquid transferring means being in contact with the respective first and second absorbent wound pads.

5. The wound dressing according to claim 4, wherein the absorbent material in the liquid transferring means comprises a hydrophilic nonwoven material.

6. The wound dressing according to claim 4, wherein the absorbent material in the liquid transferring means comprises a foam with open cells.

7. The wound dressing according to claim 4, wherein said piece of absorbent material has smaller capillaries than said first absorbent wound pad.

8. The wound dressing according to claim 1, wherein the first absorbent wound pad, when compressed, is thinner than 3 mm.

9. The wound dressing according to claim 1, wherein the first absorbent wound pad, when compressed, is thinner than 2 mm.

10. The wound dressing according to claim 1, wherein the first absorbent wound pad, when compressed, is thinner than 0.5 mm.

11. The wound dressing according to claim 1, wherein the first absorbent wound pad is made of the same material as the liquid transferring means and is made in one piece therewith.

12. The wound dressing according to claim 1, wherein the second absorbent wound pad contains super absorbent particles.

13. The wound dressing according to claim 1, wherein the second cover layer has a size allowing expansion of the second absorbent wound pad.

14. The wound dressing according to claim 1, wherein at least the first cover layer is coated by adhesive on the side thereof intended to lie against the skin of a wearer during use of the dressing.

15. The wound dressing according to claim 1, wherein a unit consisting of the second wound pad and at least a part of the second cover layer is separable from the rest of the dressing in order to allow substitution of a used such unit by a fresh such unit.

16. An article comprising a wound dressing according to claim 1 in combination with a compression bandage.

* * * * *